United States Patent [19]

Evans et al.

[11] 4,238,509

[45] Dec. 9, 1980

[54] OAT FLOUR-OIL GEL COSMETIC CREME

[75] Inventors: Gregory S. Evans, Aurora; Corinne R. Jembrzycki, Chicago, both of Ill.

[73] Assignee: Alberto-Culver Company, Melrose Park, Ill.

[21] Appl. No.: 9,341

[22] Filed: Feb. 5, 1979

Related U.S. Application Data

[63] Continuation-in-part of Ser. No. 861,832, Dec. 19, 1977, abandoned.

[51] Int. Cl.² ............................ A61K 7/00; A61K 7/48
[52] U.S. Cl. .................................... 424/358; 424/184; 424/357; 424/364; 424/365
[58] Field of Search .................... 424/70, 71, 69, 168, 424/357, 358, 364, 365, 49, 63, 64, 65, 154, 155, 184, DIG. 5

[56] References Cited

U.S. PATENT DOCUMENTS

| | | | |
|---|---|---|---|
| 2,436,818 | 3/1948 | Musher | 424/71 |
| 2,466,261 | 4/1949 | Musher | 424/364 |
| 4,014,995 | 3/1977 | Juliano | 424/69 |

*Primary Examiner*—Anna P. Fagelson
*Attorney, Agent, or Firm*—Tilton, Fallon, Lungmus & Chestnut

[57] ABSTRACT

A cosmetic creme is formed by dispersing ultra fine oat flour in a cosmetic oil gel. The creme is easily spreadable to form a thin non-greasy coating on the skin when it contains from 40 to 60% by weight of the oat flour.

9 Claims, No Drawings

OAT FLOUR-OIL GEL COSMETIC CREME

CROSS-REFERENCE

This application is a continuation-in-part of our copending application Ser. No. 861,832, filed Dec. 19, 1977 now abandoned.

BACKGROUND AND PRIOR ART

Oat flours, such as the flours prepared by grinding rolled oats, have been proposed for use in cosmetic preparations. U.S. Pat. No. 1,550,026 discloses a face pack or mask utilizing oat flour as the principal ingredient for applying an astringent to the skin. In a typical formulation, twenty ounces of oat flour are combined with three ounces of potash alum, and one ounce of casein.

U.S. Pat. No. 2,436,818 describes the incorporation of oat flour in a wide variety of cosmetic preparations, including skin lotions, cold cremes, and dentifrices. The oat flour is described as having a particle size such that 80 to 90% will pass through a 60 mesh screen. The amount of oat flour used depends on the type of preparation, up to 40% for a face mask preparation, or larger amounts for dry cosmetic preparations.

The use of ultra fine oat flours in cosmetic preparations is disclosed in U.S. Pat. No. 4,014,995. The oat flour has a particle size such that about 98% passes through a 200 mesh screen. It is stated that 1 to 20% or more of the oat flour can be used. In the formulations for cosmetic cremes disclosed in the examples, the amount of oat flour used ranges from 1 to 2%.

SUMMARY OF INVENTION

This invention is based on the discovery that ultra fine oat flour can be used to modify a cosmetic oil gel so as to substantially eliminate its oily or greasy character without interferring with the spreadability of the oil in gel form. To achieve these results, it is essential to employ a critical amount of the oat flour. The cosmetic creme which consists of a homogeneous mixture of the cosmetic oil gel with the particles of oat flour dispersed therein must contain from 40 to 60% by weight of the oat flour. With less than 40% oat flour, the preparations are oily and greasy. Above 60% oat flour, the preparations are unspreadable. Apparently the ultra fine oat flour cooperates with the gelled oil in a unique way. The resulting creme is stable, non-greasy, and readily spreadable. More specifically, the creme containing 40% to 60% oat flour is easily spreadable to form a thin non-greasy coating on the skin.

Prior art cosmetic cremes in emulsion form typically have a greasy feel on the skin when the oil content is 30% or above. Where the cosmetic creme has been formulated as a dispersion in an attempt to counteract a greasy feel, such preparations typically have been unstable because of the tendency of the dispersed particles to settle out of the preparation. In effect, therefore, the cosmetic cremes of the present invention combine the advantages of prior art high oil content emulsion cremes with those of high oil content dispersion cremes, that is, they provide both stability and reduced greasiness.

DETAILED DESCRIPTION

Cosmetic cremes can be prepared in accordance with the present invention from cosmetic oils which have been converted to gel form by an organoclay gellant (viz. a quaternary ammonium smectite). The gel may be preformed, or it may be formed as part of the preparation of the cosmetic creme. Commercially, the preformed gels are available containing hydrocarbon cosmetic oil or isopropyl myristate. While hydrocarbon cosmetic oils, isopropyl myristate, or mixtures thereof, are advantageous and preferred, other cosmetic oils can be used either in whole or in part, such as silicone cosmetic oils, triglyceride oils, such as vegetable oils, fatty acid esters, etc. Commercially available silicone cosmetic oils are polymers, viz. polydimethylcyclosiloxane (cyclomethicone). In one preferred formulation, the cosmetic oil for the creme comprises a mixture of a minor proportion of a silicone oil with a major proportion of a hydrocarbon oil and/or isopropyl myristate.

Organically-modified smectite clays, such as bentonite and hectorite, are well known gelling agents for cosmetic oils. The commercially preferred gel-forming smectite clays have been treated with a quaternary ammonium salt. The resulting cation exchange reaction produces the quaternary ammonium smectite gellant. These gellants are also commonly used in conjunction with a small amount of propylene carbonate as a wetting agent. Typically, preformed commercial gels contain about 10% gellant (quaternary ammonium bentonite or hectorite) and about 3% propylene carbonate. Other polar solvents can be used instead of propylene carbonate (ethanol, acetone, etc.). Preformed gels useable in the present invention are available from NL Industries, Inc., Industrial Chemicals Division, Hightstown, N.J.; namely, Bentone Gel MIO (mineral oil base) and Bentone Gel IPM (isopropyl myristate base).

The ultra fine oat flour for use in the cosmetic cremes of this invention can be characterized as having a particle size such that at least 98% passes through a 200 mesh screen (U.S. Sieve Series). Suitable oat flours are described in U.S. Pat. No. 4,014,995, and are available commercially from The Quaker Oats Company, Chicago, Ill., being sold under the tradenames: Oat-Pro and Ster-O-Pro. These are cosmetic grade oat flours of ultra fine particle size ($-200$ mesh). Such oat flours are made by grinding oat flakes. The cosmetic cremes of this invention consist essentially of a homogeneous mixture of the cosmetic oil bentonite gel with particles of the ultra fine oat flour dispersed therein. Critically, the creme must contain from 40 to 60% by weight of the oat flour (total creme basis). The criticality of the amount of oat flour can be seen from the experimental tests summarized below in Table A.

TABLE A

| Effect of Oat Flour on Bentone Gel | | |
|---|---|---|
| Weight % Oat Flour[1] | Weight % Bentone Gel[2] | Observations |
| 30 | 70 | greasy[3] |
| 35 | 65 | greasy |
| 40 | 60 | non-greasy,[4] thin consistency |
| 50 | 50 | non-greasy, excellent spreadability[5] |
| 60 | 40 | non-greasy, stiffer consistency, but still spreadable |
| 65 | 35 | unspreadable[6] |

TABLE A-continued

Effect of Oat Flour on Bentone Gel

| Weight % Oat Flour[1] | Weight % Bentone Gel[2] | Observations |
|---|---|---|
| 70 | 30 | unspreadable |

[1]Oat-Pro (Quaker Oats)
[2]Bentone Gel MIO (NL Industries)
[3]Appears oily and feels slick on the skin.
[4]Oily appearance and slick feel no longer present.
[5]Readily applicable to skin in thin layer.
[6]Will not spread on skin, tends to ball up and slough off.

In performing the foregoing tests, homogeneous mixtures of the proportions shown were separately applied to the skin, and rubbed with the fingers to try to spread the mixture as a thin coating.

The results obtained are believed to be surprising. Prior to the present invention, it would not have been thought possible to eliminate the greasiness of a cosmetic creme by adding oat flour thereto while still retaining spreadability. Prior art oat flour preparations containing 40% or more of oat flour have been stiff and non-spreadable, or have been in the form of powders. As far as is known, no one heretofore has combined ultra fine oat flour in any amount with a cosmetic oil gel, and there has been no recognition that the use of sufficient oat flour in a cosmetic oil gel can substantially eliminate greasiness or oiliness. As used herein, the terms "non-greasy" and "spreadable" have reference to the finding that the cremes of this invention are easily spreadable to form a thin non-greasy coating on the skin.

As an aid to practicing the present invention, a preferred formulation is set out below:

Preferred Formulation

| Ingredients | Parts by weight of creme |
|---|---|
| hydrocarbon cosmetic oil, or isopropyl myristate, or mixtures thereof | 20 to 50 |
| silicone cosmetic oil | 0 to 20 |
| quaternary ammonium smectite gellant | 3 to 5 |
| ultra fine oat flour | 45 to 55 |

In addition to the ingredients listed above, certain other minor ingredients may be incorporated. For example, from 1 to 2 parts of propylene carbonate may be incorporated as a wetting agent. As is known in the art, this will promote the formation and stability of the gel. However, the presence of propylene carbonate is not essential. As with other prior art cosmetic cremes, it would usually be desirable to add a fragrance and also a preservative. Such ingredients, however, are optional, although desirable to improve the shelf life and user acceptance of the product.

It has been found that cosmetic cremes of optimum properties are obtained when the cremes contain from 45 to 55% by weight of the ultra fine oat flour. Such preparations, as indicated, may contain a hydrocarbon oil or isopropyl myristate as the principal cosmetic oil therein. In one specific embodiment, the cosmetic oil comprises 30 to 40 parts by weight of a hydrocarbon oil or isopropyl myristate combined with 5 to 15 parts of cyclomethicone.

All the ingredients for practicing the present invention are readily available from commercial sources. Suitable commercial products are identified below in Table B.

TABLE B

| Supplier | Trade Name | CTFA Name[1] |
|---|---|---|
| Quaker Oats Co. Merchandise Mart Plaza Chicago, IL 60654 | Oat-Pro | Oat Flour (cosmetic grade) |
| | Ster-O-Pro | Oat Flour (cosmetic grade) |
| NL Industries, Inc. Industrial Chemicals Division P. O. Box 700 Hightstown, N.J. 08520 | Bentone 38 | Quaternium-18 Hectorite[2] |
| | Bentone Gel MIO | Mineral Oil (and) Quaternium-18 Hectorite (and) Propylene Carbonate |
| | Bentone 27 | Stearalkonium Hectorite[3] |
| | Bentone Gel IPM | Isopropyl Myristate (and) Stearalkonium Hectorite (and) Propylene Carbonate |
| Witco Chemicals Corp. 277 Park Ave. New York, N.Y. 10017 | Carnation White Mineral Oil | Mineral (Hydrocarbon) Oil |
| | Klearol White Mineral Oil | Mineral (Hydrocarbon) Oil |
| Armak Company Armak Ind. Chemicals Division Box 1805 Chicago, IL 60690 | Kessco Isopropyl Myristate | Isopropyl Myristate |
| Ashland Chemical Co. Div. of Ashland Oil Inc. Columbus, Ohio 43216 | Starfol IPM | Isopropyl Myristate |
| Jefferson Chemical Co. 3336 Richmond Ave. P. O. Box 53300 Houston, Texas 77052 | | Propylene Carbonate |
| Dow Corning Corp. Midland, Mich. | Dow Corning 344 Fluid | Cyclomethicone |

[1]CTFA refers to "Cosmetic, Toiletry and Fragrance Association Cosmetic Ingredient Dictionary," (2nd Edition, 1977).
[2]Reaction product of hectorite clay with dimethyl (hydrogenated tallow) quaternary ammonium chloride.
[3]Reaction product of hectorite clay with benzyl dimethyl stearyl ammonium chloride.

The cosmetic cremes of this invention are further illustrated by the following specific examples, in which certain of the ingredients are identified by the trade names set out in Table B.

EXAMPLE 1

| | % W/W |
|---|---|
| 1. Oat Flour (Oat-Pro or Ster-O-Pro) | 50.00 |
| 2. Cyclomethicone (Dow 344 Fluid) | 10.00 |
| 3. Mineral Oil | 34.68 |
| 4. Quaternium-18 Hectorite (Bentone 38) | 4.00 |
| 5. Propylene Carbonate | 1.32 |
| 6. Fragrance | q.s. |
| 7. Preservative | q.s. |

| Mixing Procedure |
|---|
| Disperse #4 in #2 & #3 till homogenous. |
| Disperse #1 in homogenous mixture. |
| Add #6 and #7. |
| Agitate mixture until smooth. |
| Add #5 and disperse well. |
| Agitate mixture until gel has formed. |

The resulting cosmetic creme is non-greasy, readily spreadable, and stable.

EXAMPLE 2

As a variation of Example 1, 40% of a preformed bentone gel is employed instead of ingredients #3, 4 and 5. The preformed gel may be Bentone Gel MIO or Bentone Gel IPM, as identified above.

EXAMPLE 3

Oat flour (Ster-O-Pro) was homogeneously dispersed in Bentone Gel MIO (Table B) to provide three test preparations as follows:

| Formula No. | % by Wt. Ster-O-Pro | % by Wt. Bentone Gel MIO |
| --- | --- | --- |
| 1 | 35 | 65 |
| 2 | 50 | 50 |
| 3 | 65 | 35 |

A perception test was conducted using 30 adults (25 women, 5 men) to compare the three formulas for non-greasiness and spreadability.

Each person evaluated each of the three formulas for non-greasiness and for ease of spreading (spreadability). Scoring was based on a 5 point system where 1=poor (greasy or non-spreadable) and 5=excellent (non-greasy or spreadable).

Approximately 150–200 mgs of each product was given to each person for evaluation. The first product was applied to the back of the left hand, rubbed in, and the evaluation scores recorded on an evaluation form. The second product was treated similarly, except for being applied to the back of the right hand. The third product was applied in the same fashion, but to the underside of the left wrist. The order in which the samples were evaluated was randomized to eliminate any bias due to the order, or site of application. The results in terms of average scores are set out below in Table C.

TABLE C

| Formula No. | Non-Greasiness | Spreadability |
| --- | --- | --- |
| 1 | 2.03 | 3.60 |
| 2 | 3.07 | 3.87 |
| 3 | 3.27 | 1.83 |

The tabulated results, as summarized in Table C, were examined for statistical significance using the Fisher distribution-free sign test and the Wilcoxon distribution-free signed rank test. The analysis confirmed that Formulas Nos. 2 and 3 were perceived as significantly (>99.7%) less greasy than Formula No. 1, while there was no difference statistically in the non-greasiness scores of Formulas Nos. 2 and 3. With reference to spreadability, Formulas Nos. 1 and 2 were preceived as significantly (>99.9%) equivalent for spreadability. It may therefore be concluded that Formula 2 is the only formula of the three tested which is perceived as both non-greasy and spreadable under the conditions of the test.

We claim:

1. A cosmetic creme which is easily spreadable to form a thin non-greasy coating on the skin, consisting essentially of a homogenous mixture of finely-divided oat flour and a non-aqueous cosmetic oil gel, said oat flour having a particle size such that at least about 98% thereof passes through a 200 mesh screen (U.S. Sieve Series), said cosmetic oil gel containing at least one cosmetic oil and a quaternary ammonium smectite gellant, said creme being characterized by containing from 40 to 60% by weight of said oat flour.

2. The cosmetic creme of claim 1 in which said creme contains from 45 to 55% by weight of said oat flour.

3. The cosmetic creme of claim 1 which contains a hydrocarbon oil as the principal cosmetic oil therein.

4. The cosmetic creme of claim 1 which contains isopropyl myristate as the principal cosmetic oil thereof.

5. A cosmetic creme which is easily spreadable to form a thin non-greasy coating on the skin, consisting essentially of finely-divided oat flour and a non-aqueous cosmetic oil gel, said oat flour having a particle size such that about 98% thereof passes through a 200 mesh screen (U.S. Sieve Series), said cosmetic oil gel being composed of:

| | ingredients | parts by weight of creme |
| --- | --- | --- |
| (a) | a cosmetic oil selected from the class consisting of a hydrocarbon cosmetic oil, isopropyl myristate, and mixtures thereof | 20 to 50 |
| (b) | a silicone cosmetic oil | 0 to 20 |
| (c) | quaternary ammonium smectite gellant | 3 to 5 | said creme being characterized by containing from 45 to 55% by weight of said oat flour.

6. The cosmetic creme of claim 5 in which said ingredient (a) is present in an amount of 30 to 40 parts by weight and said ingredient (b) is present in the amount of 5 to 15 parts by weight.

7. The cosmetic creme of claim 6 in which said ingredient (b) is cyclomethicone.

8. The cosmetic creme of claim 5 in which said ingredient (a) is a hydrocarbon oil and is present in an amount of 30 to 40 parts by weight, and said ingredient (b) is cyclomethicone and is present in an amount of from 5 to 15 parts by weight.

9. The cosmetic creme of claim 5 in which said ingredient (a) is isopropyl myristate and is present in an amount of 30 to 40 parts by weight, and said ingredient (b) is cyclomethicone and is present in an amount of from 5 to 15 parts by weight.

* * * * *